United States Patent [19]

Steigman et al.

[11] 4,406,876

[45] Sep. 27, 1983

[54] SULFUR FREE SMALL-PARTICLE PRODUCTION OF TECHNETIUM SULFUR COLLOID

[75] Inventors: Joseph Steigman; Nathan A. Solomon, both of Brooklyn, N.Y.; Lydia L. Y. Hwang, Tokyo, Japan

[73] Assignee: Research Foundation of the State Univ. of New York, Albany, N.Y.

[21] Appl. No.: 196,836

[22] Filed: Oct. 14, 1980

[51] Int. Cl.³ .................... A61K 49/00; A61K 43/00
[52] U.S. Cl. .......................... 424/1; 422/61; 424/9; 424/1.5
[58] Field of Search .............. 424/1, 1.5, 9; 422/6

[56] References Cited

U.S. PATENT DOCUMENTS

| | | | |
|---|---|---|---|
| 3,674,900 | 7/1972 | Thompson | 424/1 |
| 3,683,066 | 8/1972 | Ascanio et al. | 424/1 |
| 3,723,612 | 3/1973 | Mikheev et al. | 424/1 |
| 3,810,976 | 5/1974 | Ficken et al. | 424/1 |
| 3,862,299 | 1/1975 | Bruno et al. | 424/1 |
| 3,863,004 | 1/1975 | Wolfangel | 424/1 |
| 3,872,226 | 3/1975 | Haney et al. | 424/1 |
| 3,875,299 | 4/1975 | Winchell et al. | 424/1 |
| 3,968,221 | 7/1976 | Winchell et al. | 424/1 |
| 3,987,157 | 10/1976 | Molinski et al. | 424/1 |
| 3,992,513 | 11/1976 | Petkau et al. | 424/1 |
| 4,024,233 | 5/1977 | Winchell et al. | 424/1 |
| 4,048,296 | 9/1977 | Wolfangel | 424/1 |
| 4,066,742 | 1/1978 | Garrett | 424/1 |
| 4,071,613 | 1/1978 | Hunter, Jr. | 424/1 |
| 4,226,846 | 10/1980 | Saklad | 424/1 |
| 4,272,503 | 6/1981 | Camin et al. | 424/1 |

*Primary Examiner*—Christine M. Nucker
*Attorney, Agent, or Firm*—Omri M. Behr

[57] ABSTRACT

There is disclosed a sterile, non-pyrogenic composition and method for preparing technetium 99m colloidal material substantially free of sulfur utilized in the scanning of organs of the body.

13 Claims, No Drawings

SULFUR FREE SMALL-PARTICLE PRODUCTION OF TECHNETIUM SULFUR COLLOID

BACKGROUND OF THE INVENTION

Technetium 99m is a short-lived, radioisotope which has been found useful in radioscanning various organs of the body. Heretofore, the radioactive material has been available in colloidal form associated with sulfur. A mode of preparation is disclosed in "Preparation, Distribution and Utilization of Technetium 99m Sulfur Colloid" by Stern, H. S., McAffee, J. G. and Subramanian, G., Journal of Nuclear Medicine, 7, 665 to 675, (1966). An improvement in this basic technique is disclosed in U.S. Pat. No. 3,683,066 to Ascanio, et al. In order for the technetium 99m to be absorbed for the brief time necessary for radioscan measurements to be made it has been found necessary to administer the radio isotope in the form of a colloid as set forth in the aforementioned references. It has been found, however, that while the heretofore known colloidal compositions are useful in radioscanning certain organs, such as the liver, the colloids are not noted in other organs which should, theoretically, be examinable by this technique such as, for example, the lymph glands. There appears to be a general consensus of medical opinion that the reason for the non-appearance of the known colloids in these organs is due to a size distribution of the major component of the colloids lying above 0.1 microns in diameter.

It would therefore be desirable to provide Technetium 99m colloids whose radioactivity is substantially equal to that of the heretofore available colloids while having a size distribution wherein the major portion of the particles is 0.1 microns or less.

It should be noted that accurate measurement techniques in this particle size area which involves light scattering measurements are expensive and not readily available. The smallest practical readily available ultrafilter will block the passage of particles greater than 0.1 micron in diameter. It is known, however, that a Sephadex G-25-80 gel column will only permit the passage of colloidal material substantially smaller than 0.1 microns in diameter. The exact size range of these particles has not been determined, however, all have the ability to pass through a 0.1 micron ultrafilter. This practical though by no means arbitrary method is utilized herein as the criterion of size measurement.

All of the work done heretofore on technetium 99m colloids has assumed that it was necessary for the sulfur to be associated with the technetium 99m. It was further generally assumed, though never clearly proved, that the technetium was in some way deposited upon the surface of the colloidal sulfur and hence clearly the sulfur was an essential and irremovable part of the colloidal system.

It has also been known (see for example U.S. Pat. No. 3,683,066, column 2, lines 23 through 25) that the presence of a gelling agent such as gelatin is important as a growth inhibiting and colloid stabilizing reagent. In addition to the named gelatin, other agents, including bovine serum albumin, are known as suitable agents however heretofore there has been no reason to consider one of these agents superior in action to any other.

SUMMARY OF THE INVENTION

It has been the surprising finding of the present invention that, contrary to what had previously been assumed, technetium 99m colloid when produced by the methods of the prior art is not absorbed upon sulfur but rather the sulfur is absorbed upon the technetium 99m colloid. A method is therefore provided to remove the sulfur formed in accordance with the methods of the prior art while leaving intact a technetium colloid of substantially the same level of radioactivity as heretofore but wherein the vast majority of the particles have a size of less than 0.1 microns (by Sephadex gel filtration). Furthermore, there is provided a method of providing technetium 99m colloids of the foregoing size distribution which may be readily produced in a manner which co-produces a minimal amount of sulfur colloid.

It has further been surprisingly found that substantially superior results are obtained by utilizing bovine serum albumin rather than gelatin as the growth inhibiting and colloid stabilizing reagent in the reaction.

In the standard technique (i.e., U.S. Pat. No. 3,683,066) the final stage of the preparation calls for the provision of an alkaline buffer solution which raises the pH of the colloid to 6 or more suitably to 6.2 during the cooling step of the formation. It has been found that the sulfur content of the thus produced colloidal material can be substantially eliminated by subjecting the thus produced mixture to somewhat more vigorous reaction conditions at this pH level or greater, suitably by heating. It will be understood by those skilled in the art that an increase in temperature at a low pH (within this range) will require a shorter reaction time for the desired effect than carrying out the reaction at that pH range at lower temperatures. Similarly, carrying out the reaction at higher pH levels would also require shorter reaction times at a given temperature than at the lower end of the pH range. Equally, it will be understood by those skilled in the art that subjecting a colloid either to high temperatures or high pH for a substantial length of time will ultimately destroy the colloidal character of the suspension. Thus, suitably, the reaction conditions are chosen so as to provide that the major portion, say more than 60% of the colloidal particles have a diameter of less than 0.1 microns.

The inter-reaction of the ions produced by a combination of sulfur and oxygen upon sulfur and upon metallic ions at acid pH levels is extremely complex and not totally understood. At pH levels of 6 or above it is believed that the following reaction takes place
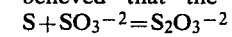
$S + SO_3^{-2} = S_2O_3^{-2}$ There is, however, substantial teaching in the art which calls into question the stability of technetium sulfide colloids in the presence of alkali. Again, while the actual chemistry involved in the formation of sulfur colloids by the action of acid, suitably hydrochloric acid, upon alkali metal thiosulfates such as sodium thiosulfate, is extremely complex and not fully understood, the presence of bisulfite ions suitably sodium bisulfite in the reaction mixture of, say, Ascanio, has been noted. Thus, it has been found that where a product such as that obtained by Ascanio has not been further treated to remove the bisulfite, the sulfur colloids can be removed by conversion into a sulfur/oxygen ion merely by heating for a suitable time or heating in conjunction with raising the pH by any suitable means.

It has further been found that when the procedures of the prior art, for example, those disclosed by Ascanio are carried out but where in place of thiosulfate there is used trithionate, there is obtained technetium colloid having suitably the desired particle distribution but containing less than 10% of sulfur colloid. Where this reagent is used therefore it is not necessary to subject the product to the sulfur removal procedures set forth above, although they may be employed to remove the small amounts of sulfur produced by a different reaction.

Where there is provided a technetium sulfur colloid not in the presence of bisulfite ion, a sufficient quantity of bisulfite must be added in accordance with the foregoing equation and the mixture heated at raised pH in the manner set forth above.

DESCRIPTION OF THE PREFERRED EMBODIMENTS

In one embodiment of the present invention, a technetium sulfur colloid is produced in accordance with Examples 1 and 2 of U.S. Pat. No. 3,683,066 the disclosure of which is incorporated herein by reference.

The mixture obtained in accordance with Example 2 of the patent has a pH of approximately 6. The resultant mixture is then heated at a predetermined time at a predetermined pH of this level or higher, the pH having been adjusted, if necessary, by the addition of aqueous alkali suitably aqueous sodium hydroxide. Heating may range from ten minutes to one hour depending upon pH levels and the pH range itself may be set between about 6 to about 12.

Thus at pH 6.2 heating at bath temperature of approximately 100° C. for ten minutes will suffice. At a pH level of between 7.5 to 8.5 five minutes at this temperature is adequate, while two minutes at pH 9.5 produces excellent results. At pH 11 for ten minutes acceptable results were still obtained however the quantity of colloidal material began to decline. Where the heating is at 50° C. at approximately pH 6 thirty minutes are adequate. Similar results were obtained at pH 10.5 and no improvement noted after a further 1.5 hours. Mere pH adjustment to 11.5 without heating gave satisfactory results after one hour with very slight improvement after four hours.

The mode of preparation of the substantially sulfur-free technetium 99m colloid utilizing trithionate and pentathionate or the like in place of thiosulfate is carried out substantially in the same way.

The use of trithionate or the like in place of thiosulfate reduces the sulfur initially generated very substantially, from about 100 micrograms of sulfur per ml (method of Ascanio) to about 8 micrograms/ml. However, this level can be even further reduced. The addition of sulfite is not necessary though not disadvantageous, however reincubation suitably with some degree of heating is useful to even further reduce the sulfur content to a negligible amount. Similar conditions of pH and incubation temperature hold here as in the thiosulfate case. However, where trithionate or the like is utilized, while the process is operative at a pH level over 10, the amount of colloid produced starts to fall off at pH levels above 8, thus an incubation pH of approximately 8 at about 100° C. for about 5 minutes appears to be a very desirable reaction condition. Similarly, it has been found that higher concentrations of trithionate give rise to larger particles of technetium colloid. Thus Ascanio teaches concentration levels of sodium thiosulfate of the order of 0.8 mg/ml prior to addition of buffer. Where trithionate is utilized while the process is operative at levels exceeding 0.3 mg/ml optimum results are obtained at or below this concentration.

It has also been found that not only is removal of residual sulfur effected by the incubation at a pH level of about 8 at ambient temperature, but a short incubation suitably from about 2 to about 10 minutes preferably about 5 minutes at 100° C. bath produces both a larger percentage of colloid and a larger proportion of that colloid having a mean diameter of less than 0.1 microns.

While both gelatin and serum albumin, suitably human or bovine serum albumin, are operative as growth inhibiting and colloid stabilizing reagents in both of the embodiments of the present invention discussed hereinabove, the proportion of colloid having a diameter less than 0.1 microns (by the sephadex gel standard) is approximately twice as great when serum albumin is the gelling agent than when gelatin is the gelling agent. This particular advantage only becomes apparent in procedures where the sulfur particles are either removed or substantially prevented from forming.

All experiments were performed utilizing a commercially available kit for the provision of 99m technetium sulfur colloid. Tesuloid (Registered trademark of Squibb and Co.)

EXAMPLES

Standard Preparation

To a solution of sodium thiosulfate (3 ml containing 12 mg) is added aqueous hydrochloric acid (1.5 ml, 1M) and 1 ml of a mixture comprising gelatin (9 mg/ml), $K_2HPO_4$ (25.5 mg/ml) and $Na_2EDTA$ (2.8 mg/ml). Pertechnetate 99m (0.2 ml) is added thereto and the mixture is diluted to 10 ml with sterile water and heated at a bath temperature of 100° C. for 10 minutes, the mixture is cooled substantially to ambient temperatures and a buffer solution, 1 ml, of $NaH_2PO_4$ 70 mg/ml and NaOH 20 mg/ml are added. This raises the pH substantially to 6.2.

The foregoing standard mixture is either heated again (second incubation) at that pH for varying lengths of time at different temperatures or this heating is carried out after the addition of sufficient alkali, suitably NaOH to raise the pH to a predetermined level. The results obtained are set forth in Table 1; unless otherwise stated all technetium is in the form of particles.

In the trithionate experiments, sodium trithionate is substituted for sodium thiosulfate. Particle size is measured by initial passage through a 0.1 micron ultrafilter.

TABLE 1

| pH | Temperature (bath) | Time (min) | % Particles <0.1μ | Comments |
|---|---|---|---|---|
| 6.2 | 100° C. | 2 | 22% | (mean 0.5–0.3μ) |
| 6.2 | 100° C. | 20 | >76% | |
| 7.5/8.5 | 100° C. | 5 | >80% | |
| 7.5/8/5 | 100° C. | 10 | >80% | |
| 9.5 | 100° C. | 2 | 99% | No $TcO_4^-$ |
| 11 | 100° C. | 10 | 99% | 13% $TcO_4^-$ |
| 11 | 100° C. | 11.6 | 99% | 21% $TcO_4^-$ |
| 6.2 | 50° C. | 30 | 20% | (mean 0.5–0.3μ) |
| 6.2 | 50° C. | 180 | 24% | Further size reduction |
| 10.5 | 50° C. | 30 | 80% | |
| 10.5 | 50° C. | 180 | 80% | |
| 11.5 | 20° C. | 60 | 80% | |
| 11.5 | 20° C. | 240 | 85% | |

SULFUR ANALYSIS (a) Standard mixture was prepared to pH 6.2, pH raised to pH 9 and heated for 5 minutes at that pH per se and in the presence of additional sodium bisulfite (100 mg/200 ml mix).

(b) Using standard mixture to pH 6.2 but substituting 3 mg/10 ml of sodium trithionate for the sodium thiosulphate in acid for 40 minutes first incubation at 100° C. Thereafter, heating for 10 minutes at pH 8.2 per se and sodium bisulfite as above.

|   |   | Orig. Mix. | After heating at (a) pH for 5 minutes (b) pH 8.2 for 10 minutes | |
|---|---|---|---|---|
|   |   |   | w/o bisulfite | with bisulfite |
| a | μg/ml S | 93 | .23 | .006 |
|   | % S of orig. mix. |   | .25 | .06 |
| b | μg/ml S |   | 0.42 | 0.42 |

EFFECT OF GELATIN

The procedure of Example I is repeated utilizing no gelatin, utilizing the gelatin concentration of Example I, and using 5 times this gelatin concentration.

Particles passing through a 0.1 micron ultrafilter
(a) without gelatin 21%
(b) with standard gelatin concentration 73%
(c) with 5 times standard gelatin 91%

In accordance with the procedure of Example I but where bovine serum albumin is utilized in place of gelatin, after the step of heating at 100° C. for 10 minutes (as in the procedure of Example I), the mixture is cooled for 5 minutes, buffered to pH 8.9, reincubated for 5 minutes at 100° C. (bath) and cooled. Percentage of particles passing through a 0.1 micron ultrafilter and through a Sephadex G-25-80 column: 90%

UTILIZATION OF SODIUM TRITHIONATE

The procedure of Example I was followed except that sodium trithionate was substituted for sodium thiosulfate.

| Trithionate Conc. | .6 mg/ml | 1.2 mg/ml | 2.4 mg/ml | 6 mg/ml |
|---|---|---|---|---|
| % Particles <0.1μ | 77 | 58 | 44 | 35 |
| % TcO4 | 14 | 3.2 | 1.4 | 1.3 |
| % of Total technitium which passed through Sephadex column | 37 | 38 | 29 | 15 |

ANIMAL TESTS

A sample of technetium 99m colloid was prepared with bovine serum albumin in accordance with the above Example. A further sample of antimony sulfide/technetium 99m colloid (O. L. Garzon, M. C. Palcos, and R. Radicella, International Journal of Applied Radiation and Isotopes 16, 613 (1965), was also prepared. The samples were injected into two Chihuahua dogs and isotopic lymphangiograms taken. In both instances lymph node activity was noted as well as liver and spleen activity. The antimony preparation appears to have more blood pool activity than the technetium colloid of the present invention whereas the latter has some activity in the salivary glands. Both preparations indicated satisfactory results for lymphangiography.

We claim:

1. A kit for the preparation of technetium 99m colloid substantially free of sulfur which comprises, in separate containers:
   a. a reagent containing a gelling agent and an alkali metal thiosulfate;
   b. a buffer solution;
   c. an acid solution;
   d. an alkali; and
   e. a chelating agent put in any of the containers of a, b, c above to prevent flocculation.

2. A process for the preparation of technetium 99m colloid substantially free of sulfur which comprises the steps of:
   a. providing pertechnetate to a reagent mixture comprising a gelling agent and alkali metal thiosulfate, and acid and a chelating agent,
   b. heating the mixture
   c. cooling the mixture and adding a buffer thereto to bring the pH to a value of at least 6;
   d. reheating the mixture.

3. A process of claim 2 comprising adding sufficient buffer at step c. to raise the pH to between 6 and 12 and heating the mixture to a temperature between ambient temperature and 100° C. for a sufficient time to provide a substantially sulfur-free technetium 99m colloid suspension having at least 60% of the particles in a size range of less than 0.1 microns.

4. A process according to claim 3 wherein the gelling agent is gelatin or serum albumin.

5. A process according to claim 4 wherein the gelling agent is serum albumin.

6. A process of removing substantially all of the sulfur content from a colloidal suspension of technetium 99m colloid in the presence of a sulfur colloid suspension containing bisulfate ions comprising adding sufficient buffer to raise the pH to between 6 and 12 and heating the mixture to a temperature between ambient temperature and 100° C. for a sufficient time to provide a substantially sulfur-free technetium 99m colloid suspension.

7. A process of claim 6 wherein there is produced a suspension having at least 60% of the particles in a size range of less than 0.1 microns.

8. A process of removing substantially all of the sulfur content from a colloidal suspension of technetium 99m colloid, substantially free of bisulfite ion, in the presence of sulfur colloid comprising the steps of adding sufficient sulfite ion to react with the sulfur present and adding sufficient alkali to raise the pH to between 6 and 12 and heating the mixture to a temperature between ambient temperature and 100° C. for a sufficient time to provide a substantially sulfur-free technetium 99m colloid suspension.

9. A process of claim 6 wherein there is produced a suspension having at least 60% of the particles in a size range of less than 0.1 microns.

10. A kit for the preparation of technetium 99m colloid substantially free of sulfur which comprises, in separate containers:
    a. a reagent containing a gelling agent and an alkali metal trithionate;
    b. a buffer solution;
    c. an acid solution;
    d. an alkali; and e. a chelating agent put in any of the containers of a, b, c above to prevent flocculation;

put in any of the containers of a, b, or c above to prevent flocculation.

11. A process for the preparation of technetium 99m colloid substantially free of sulfur which comprises the steps of:

a. providing pertechnetate to a reagent mixture comprising a gelling agent and alkali metal trithionate, and acid and a chelating agent;
b. heating the mixture;
c. cooling the mixture and adding a buffer thereto to bring the pH to a value of at least 6;
d. reheating the mixture.

12. A process according to claim 11 wherein the gelling agent is gelatin or serum albumin.

13. A process according to claim 12 wherein the gelling agent is serum albumin.

* * * * *